United States Patent [19]

Rechnitz et al.

[11] 4,216,065
[45] Aug. 5, 1980

[54] BIO-SELECTIVE ELECTRODE PROBES USING TISSUE SLICES

[75] Inventors: Garry A. Rechnitz; Mark A. Arnold; Mark E. Meyerhoff, all of Newark, Del.

[73] Assignee: University of Delaware, Newark, Del.

[21] Appl. No.: 49,092

[22] Filed: Jun. 18, 1979

[51] Int. Cl.² ............................................. G01N 27/46
[52] U.S. Cl. ................................ 204/1 T; 204/195 B; 204/195 P
[58] Field of Search ............... 204/1 T, 195 B, 195 M, 204/195 P, 296; 23/230 B; 424/12; 195/103.5 R, 103.5 C; 428/213; 156/230; 210/490, 500 M

[56] References Cited

U.S. PATENT DOCUMENTS

| | | | |
|---|---|---|---|
| 3,098,813 | 7/1963 | Beebe et al. | 204/195 P |
| 3,575,836 | 4/1971 | Sternberg | 204/195 P |
| 3,776,819 | 12/1973 | Williams | 204/195 B |
| 3,966,580 | 6/1976 | Janata et al. | 204/195 B |
| 3,979,274 | 9/1976 | Newman | 204/195 B |

*Primary Examiner*—Arthur C. Prescott

[57] ABSTRACT

A bio-selective potentiometric electrode probe for the determination of amino acid concentrations in aqueous liquids comprising an ammonia gas analytical electrode provided at its tip with a closely adjacent thin layer of a fresh animal tissue containing, as a natural constituent thereof, an enzyme effective to catalyze degradation of the specific amino acid in analysis to either ammonia or to an intermediate compound subject to further degradation to ammonia by an additional enzyme, which ammonia is a function of the amino acid concentration in the liquid.

6 Claims, 3 Drawing Figures

□ – glutamine    ● – $NH_3$

BIO-SELECTIVE ELECTRODE PROBES USING TISSUE SLICES

GENERAL

The research culminating in this invention was conducted under National Science Foundation Grant No. CHE-7728158 and National Institutes of Health Grant No. GM-25312, pursuant to which the Government possesses certain property rights.

BACKGROUND OF THE INVENTION

It is frequently necessary to measure the concentrations of individual amino acids in either clear or turbid solutions in aqueous liquids, including physiological fluids such as blood serums and spinal fluids. This has proved difficult or even impossible to achieve with existing technology. However, two of the present inventors have achieved success in this regard by the use of membrane electrodes utilizing living bacterial cells, as described in their publication *Science*, vol. 199, pp. 440–41 (1978), authors Rechnitz, Riechel, Kobos and Meyerhoff.

SUMMARY OF THE INVENTION

This invention comprises a bio-selective potentiometric electrode probe for determination of the concentrations of preselected individual amino acids in aqueous liquids comprising an ammonia gas analytical electrode equipped with a gas-permeable membrane provided at its tip with a closely adjacent thin layer of a fresh animal tissue containing, as a natural constituent thereof, a preselected enzyme effective to catalyze degradation of the amino acid in analysis to either ammonia or to an intermediate compound subject to further degradation to ammonia in the presence of an additional preselected enzyme, which ammonia is a function of the amino acid concentration in the aqueous liquid.

DRAWINGS

The following drawings constitute part of this disclosure, in which:

FIG. 1A is a schematic longitudinal cross-sectional view of the electrode tip region of a preferred embodiment of this invention;

FIG. 1B is an exploded view of the several components of the embodiment of FIG. 1A which illustrates the analytical operation thereof; and FIG. 2 is a typical calibration curve for an electrode constructed according to this invention for the analysis of L-glutamine utilizing pork kidney tissue as the biocatalytic medium, in terms of mV electrode response on the ordinate vs. —log concentration, M, of the substrate (sample) in test as abscissa.

DETAILED DESCRIPTION OF THE INVENTION

Figure 1A:
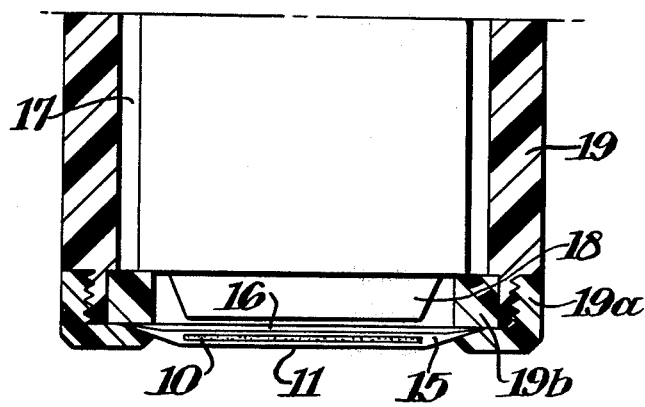
Figure 1B:
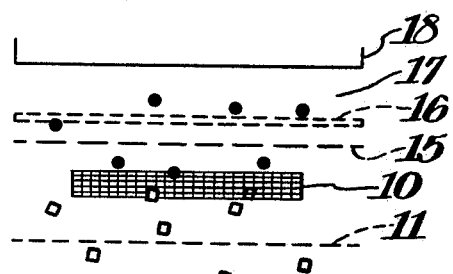

Referring to FIGS. 1A and 1B, there is shown in longitudinal cross-section the tip region of a conventional ammonia gas sensing electrode, e.g., an Orion Model 95–10. This electrode comprises a polymeric body tube 19 threaded at the outboard end to accept an annular screw cap 19a.

As marketed, the electrode is provided with gas-permeable membrane 16, maintained in place against base ring 19b by the compression of screw cap 19a, internal electrolyte solution 17, and pH sensing glass membrane 18.

In the practice of this invention, catalytic degradation of amino acid in clear or turbid aqueous medium samples is achieved by attaching, in the tip region of the electrode, a thin layer 10 of the fresh animal tissue containing, as a natural constituent thereof, a preselected enzyme effective to catalyze degradation of the amino acid in analysis to either ammonia or to an intermediate compound subject to further degradation to ammonia in the presence of an additional preselected enzyme. Conveniently, tissue layer 10 is maintained snugly against the electrode tip of FIG. 1A by a piece of monofilament nylon mesh 11, (mesh size typically 105 microns) which is secured in place by assembly under screw cap 19a. It is not essential that tissue layer 10 overlie the entire open area of base ring 19b, good results being achieved where the tissue layer approximates the pH sensing glass membrane 18 tip area and is generally aligned therewith. Protective dialysis membrane 15 is interposed between tissue slice 10 and gas-permeable membrane 16, as it has been found that tissue slice 10 otherwise causes deterioration of membrane 16 over a prolonged period.

In the analysis of the amino acid glutamine, we have found that pork kidney possesses high glutaminase activity which rapidly degrades glutamine to products including ammonia, thereby permitting direct amino acid concentration determination without the necessity for additional enzyme supplementation.

The kidney tissue is obtained in the fresh state from hogs immediately after their slaughter from the cortex region of the kidney, the thickness typically being approximately 0.05 mm and a typical size of 12 mm diameter. Pork kidneys are preferably stored at 4° C. before use. Dialysis membrane 15 typically has a molecular weight cutoff of about 12,000. If desired, a dialysis membrane of the same characteristics as membrane 15 can be substituted for nylon mesh 11 as the retainer for tissue slice 10.

The potentiometric response of the kidney slice electrode was evaluated at 26° C. in 0.1 M phosphate buffer, pH 7.8, containing 0.02% sodium azide as preservative. The response to buffer solely is that indicated by the horizontal line to the right of point O, upper right hand portion of FIG. 2, and this constitutes the background potential. Between experiments, the electrodes were stored in the buffer at room temperatures.

Figure 2:
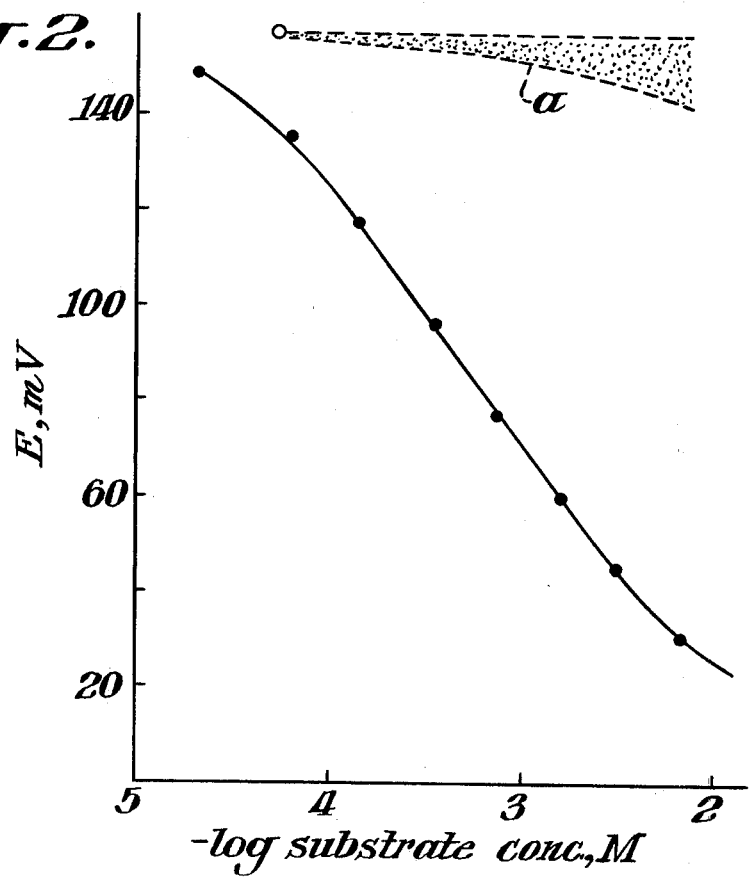

FIG. 2, full line plot, is a typical calibration curve of the electrode for L-glutamine. The slope, linear range and detection limit remain unchanged over at least 28 days of electrode use. Typically, 5–7 minutes are required for the electrode to attain a steady potential value after each addition of glutamine to the test solution.

The kidney tissue electrode yielded negligible response to such possible interferents as urea, L-alanine, L-arginine, L-histidine, L-valine, L-serine, L-glutamic acid, L-aspargine, L-aspartic acid, D-alanine, D-aspartic acid, glycine and creatinine. The dotted plot at the upper right-hand section of FIG. 2 represents the maximum response (curve a) to the thirteen possible interferents tested. It will be seen from curve a that, in terms of equivalent glutamine, the maximum interference which can possibly exist is approximately two and one half orders of magnitude less than a given glutamine concentration, so that, practically, there is no interference problem.

In service, potentiometric measurements are conducted in the conventional manner using a commercially available pH meter or similar device. Thermostating of samples is desirable. An acceptable procedure involves placing 10–25 ml of the glutamine-containing sample into the thermostated cell, stirring and thereafter immersing the electrode probe. A steady potential is normally reached in 5–10 minutes. Calibration curves are prepared using known standards, and the pH should be held constant throughout. A pH of about 7.8 is optimal. Between measurements, the electrode is returned to the buffer solution to stabilize the background potential.

The quantitative relationship of sensed potential to $NH_3$ concentration is expressed by the following equation:

$$E = E_o - 59.1 \text{ (log NH}_3 \text{ concentration, M)}$$

where $E$ = the sensed potential in mV, and
$E_o$ = the background (buffer potential)

As shown in FIG. 2, the electrode probe hereinbefore described can measure glutamine over the concentration range of at least $10^{-2}$ to $5 \times 10^{-5}$ molar with response slopes of approximately 53 mV per 10-fold concentration change. When prepared from fresh pork kidney, the electrode displays good selectivity for glutamine over other amino acids and over substances such as urea.

As another example, an arginine sensing electrode was prepared using a beef liver slice as the tissue layer 10. This electrode is more complex than the glutamine electrode because the beef liver enzyme arginase carries the degradation of arginine only to urea, which must then be finally degraded to ammonia by supplementation with the enzyme urease.

The arginine electrode is constructed exactly as described for the glutamine electrode of FIGS. 1A and 1B, except that assembly is completed with a second dialytic membrane (replacing nylon mesh 11) mounted outboard of the elements shown in FIG. 1A and interfacing with the test solution. A few drops of the supplemental enzyme urease are applied to the outward face of the beef liver tissue and the second dialytic membrane maintains it in place and against loss to the solution.

We have found that a suitable buffer solution for the arginine electrode is 0.2 molar tris HCl having a pH of 8.5.

By way of comparison, parallel electrode experiments were conducted using the isolated porcine kidney glutaminase enzyme (Sigma, grade VI) known to be thermally unstable. Small volumes (approx. 15 μl) of enzyme suspension were immobilized at the surface of the ammonia gas sensing electrode by means of a dialysis membrane and electrode response toward L-glutamine was evaluated in the buffer medium.

Freshly prepared enzyme electrodes yielded moderate potentiometric response (e.g., 44 millivolts per tenfold change in substrate concentration) but lost more than 50% of their activity within two days, and showed negligible response after four days at room temperature. Thus, it is clear that the kidney tissue electrode affords a very substantial improvement in terms of both lifetime and response, over the conventional enzyme electrode.

It is clear that other tissue-based electrodes can be readily prepared for the concentration determination of yet other specific amino acids using the teachings of this invention, and no limitations are intended beyond those of the appended claims.

What is claimed is:

1. A bio-selective potentiometric electrode probe equipped with a gas-permeable membrane for the determination of the concentration of a preselected amino acid in an aqueous liquid comprising an ammonia gas analytical electrode provided at its tips with a closely adjacent thin layer of a fresh animal tissue containing, as a natural constituent thereof, a preselected enzyme effective to catalyze degradation of said amino acid in analysis to either ammonia or to an intermediate compound subject to further degradation to ammonia in the presence of an additional preselected enzyme, which ammonia is a function of said preselected amino acid concentration in said aqueous liquid, and a dialytic membrane interposed between said gas-permeable membrane and said animal tissue layer.

2. A bio-selective potentiometric electrode probe for the determination of the concentration of a preselected amino acid in an aqueous liquid according to claim 1 wherein said thin layer of said fresh animal tissue and said additional preselected enzyme are both retained closely adjacent said ammonia gas electrode tip by a second dialysis membrane interfacing with said amino acid-containing aqueous liquid.

3. A bio-slective potentiometric electrode probe for the determination of the concentration of glutamine in an aqueous liquid according to claim 1 wherein said fresh animal tissue is a thin slice of pork kidney excised from the cortex region.

4. A bio-selective potentiometric electrode probe for the determination of the concentration of arginine in an aqueous liquid medium according to claim 2 wherein said fresh animal tissue is a thin slice of beef liver and said additional preselected enzyme is urease.

5. In the potentiometric determination of the concentration of a preselected amino acid in an aqueous liquid utilizing an ammonia gas analytical electrode fitted with a gas-permeable membrane having its tip immersed in said aqueous liquid, the improvement comprising maintaining closely adjacent said electrode tip but separated therefrom and from said gas-permeable membrane by a dialytic membrane, a thin layer of a fresh animal tissue containing, as a natural constituent thereof, a preselected enzyme effective to catalyze degradation of said amino acid in analysis to either ammonia or to an intermediate compound subject to further degradation to ammonia in the presence of an additional preselected enzyme, which ammonia is a function of said preselected amino acid concentration in said aqueous liquid.

6. The method of potentiometric determination of the concentration of a preselected amino acid in an aqueous liquid according to claim 5 wherein said thin layer of said fresh animal tissue and said additional preselected enzyme are both retained adjacent said electrode tip by a second dialysis membrane interfacing with said amino acid-containing aqueous liquid.

* * * * *